United States Patent
Moeck et al.

(10) Patent No.: US 9,775,878 B2
(45) Date of Patent: Oct. 3, 2017

(54) METHODS FOR TREATING BACTERIAL INFECTIONS USING ORITAVANCIN AND POLYMYXINS

(71) Applicant: The Medicines Company, Parsippany, NJ (US)

(72) Inventors: Gregory Moeck, St. Laurent (CA); Francis Arhin, Laval (CA)

(73) Assignee: THE MEDICINES COMPANY, Parsippany, NJ (US)

( * ) Notice: Subject to any disclaimer, the term of this patent is extended or adjusted under 35 U.S.C. 154(b) by 0 days.

(21) Appl. No.: 14/914,773

(22) PCT Filed: Aug. 28, 2014

(86) PCT No.: PCT/US2014/053093
§ 371 (c)(1),
(2) Date: Feb. 26, 2016

(87) PCT Pub. No.: WO2015/031579
PCT Pub. Date: Mar. 5, 2015

(65) Prior Publication Data
US 2016/0206687 A1    Jul. 21, 2016

Related U.S. Application Data

(60) Provisional application No. 61/871,242, filed on Aug. 28, 2013.

(51) Int. Cl.
*A61K 38/14*    (2006.01)
*A61K 38/12*    (2006.01)

(52) U.S. Cl.
CPC .............. *A61K 38/14* (2013.01); *A61K 38/12* (2013.01)

(58) Field of Classification Search
CPC ................................ A61K 38/12; A61K 38/14
See application file for complete search history.

(56) References Cited

U.S. PATENT DOCUMENTS

| | | | | |
|---|---|---|---|---|
| 2011/0201546 A1* | 8/2011 | Lehoux | ................ | A61K 38/14 514/2.6 |
| 2014/0162937 A1* | 6/2014 | Vaara | .................... | A61K 38/12 514/2.8 |
| 2016/0101148 A1* | 4/2016 | Moeck | ................ | A61K 9/0019 514/2.7 |

FOREIGN PATENT DOCUMENTS

WO    2014/188178    11/2014

OTHER PUBLICATIONS

Moellering "Antimicrobial Synergism: An Elusive Concept " J Infectious Disease (1979) 140, pp. 639-641).*
Yoshida et al. "Potent in Vitro Bactericidal Activity of Polymyxin B against Methicillin-Resistant *Staphylococcus aureus* (MRSA)," Microbiol. Immunol. (1993), 37(11), 853-859.*
Gordon et al. "Potent Synergy and Sustained Bactericidal Activity of a Vancomycin-Colistin Combination versus Multidrug-Resistant Strains of Acinetobacter baumannii," Antimicrobial Agents Chemotherapy (2010) 54, pp. 5316-5322.*
Belley et al. "Assessment by Time-Kill Methodology of the Synergistic Effects of Oritavancin in Combination with Other Antimicrobial Agents against *Staphylococcus aureus*" Antimicrobial Agents and Chemotherapy (2008) 52, 3820-3822.*
Extended European Search Report issued Mar. 15, 2017 in corresponding European Application No. 14840699.4.

* cited by examiner

*Primary Examiner* — Christina Bradley
(74) *Attorney, Agent, or Firm* — Wenderoth, Lind & Ponack, L.L.P.

(57) ABSTRACT

Methods of treating bacterial infections in a subject using a synergistic combination of oritavancin and a polymyxin are disclosed.

19 Claims, 2 Drawing Sheets

ORI, oritavancin; COL, colistin

B.

ORI, oritavancin; COL, colistin

Figure 1C

ORI, oritavancin; COL, colistin

METHODS FOR TREATING BACTERIAL INFECTIONS USING ORITAVANCIN AND POLYMYXINS

TECHNICAL FIELD

The invention relates to methods of treating bacterial infections in a subject using a synergistic combination of antibacterial agents.

BACKGROUND

Oritavancin diphosphate (oritavancin; also known as $N^{DISACC}$-(4-(4-chlorophenyl)benzyl)A82846B and LY333328) is a semi-synthetic lipoglycopeptide derivative of a naturally occurring glycopeptide. Its structure confers potent antibacterial activity against gram-positive bacteria, including vancomycin-resistant *enterococci* (VRE), methicillin- and vancomycin-resistant staphylococci, and penicillin-resistant *streptococci*. The rapidity of its bactericidal activity against exponentially-growing *S. aureus* ($\geq$3-log reduction within 15 minutes to 2 hours against MSSA, MRSA, and VRSA) is one of the features that distinguishes it from the prototypic glycopeptide vancomycin (McKay et al., *J Antimicrob Chemother.* 63(6):1191-9 (2009), Epub 2009 Apr. 15).

Oritavancin inhibits the synthesis of peptidoglycan, the major structural component of the bacterial cell wall by a mechanism that is shared with glycopeptides, such as vancomycin (Allen et al., *Antimicrob Agents Chemother* 41(1): 66-71 (1997); Cegelski et al., *J Mol Biol* 357:1253-1262 (2006); Arhin et al., Poster C1-1471: Mechanisms of action of oritavancin in *Staphylococcus aureus* [poster]. 47th Intersci Conf Antimicro Agents Chemo, Sep. 17-20, 2007, Chicago, Ill.). Oritavancin, like vancomycin, binds to the Acyl-D-Alanyl-D-Alanine terminus of the peptidoglycan precursor, lipid-bound N-acetyl-glucosamine-N-acetyl-muramic acid-pentapeptide (Reynolds, *Eur J Clin Microbiol Infect Dis* 8(11):943-950 (1989); Nicas and Allen, Resistance and mechanism of action. In: Nagarajan R, editor. *Glycopeptide antibiotics*. New York: Marcel Dekker 195-215 (1994); Allen et al., *Antimicrob Agents Chemother* 40(10):2356-2362 (1996); Allen and Nicas, *FEMS Microbiology Reviews* 26:511-532 (2003); Kim et al., *Biochemistry* 45:5235-5250 (2006)). However, oritavancin inhibits cell wall biosynthesis even when the substrate is the altered peptidoglycan precursor that is present in VRE and vancomycin-resistant *S. aureus* (VRSA). Thus, the spectrum of oritavancin antibacterial activity extends beyond that of vancomycin to include glycopeptide-resistant *enterococci* and staphylococci (Ward et al., *Expert Opin Investig Drugs* 15:417-429 (2006); Scheinfeld, *J Drugs Dermatol* 6:97-103 (2007)). Oritavancin may inhibit resistant bacteria by interacting directly with bacterial proteins in the transglycosylation step of cell wall biosynthesis (Goldman and Gange, *Curr Med Chem* 7(8):801-820 (2000); Halliday et al., *Biochem Pharmacol* 71(7):957-967 (2006); Wang et al., Poster C1-1474: Probing the mechanism of inhibition of bacterial peptidoglycan glycotransferases by glycopeptide analogs. 47th Intersci Conf Antimicro Agents Chemo, Sep. 17-20, 2007). Oritavancin also collapses transmembrane potential in gram positive bacteria, leading to rapid killing (McKay et al., Poster C1-682: Oritavancin disrupts transmembrane potential and membrane integrity concomitantly with cell killing in *Staphylococcus aureus* and vancomycin-resistant *Enterococci*. 46th Intersci Conf Antimicro Agents Chemo, San Francisco, Calif., Sep. 27-30, 2006). These multiple effects contribute to the rapid bactericidal activity of oritavancin.

Polymyxins are polypeptide antibiotics that include five chemically different compounds (Polymyxins A-E) (Balaji V et al., Polymyxins: Antimicrobial susceptibility concerns and therapeutic options. *Indian J Med Microbiol* 2011; 29:230-42). Polymyxin B was first isolated in Japan in 1949 and it is derived from *Bacillus polymyxa*. Polymyxin E, also known as colistin, can be obtained from *Bacillus polymyxa* subspecies *colistinus*. Polymyxins B and E have both been used in clinical practice for over 50 years, while polymyxin A, C and D are not used to treat humans because of toxicity concerns. Polymyxin E (colistin) was initially used in intravenous and intramuscular formulations for the treatment of gram-negative bacterial infections, falling out of favor in the 1970s upon the introduction of aminoglycosides which exhibit less toxicity.

Polymyxins are surface-acting ampipathic agents (Balaji V. et al., Polymyxins: Antimicrobial susceptibility concerns and therapeutic options. *Indian J Med Microbiol* 2011; 29:230-42). Each molecule of polymyxin includes a cationic polypeptide ring with a lipophilic fatty acid side chain (Kwa A L et al., Polymyxins: A review of the current status including recent developments. *Ann Acad Med Singapore* 2008; 37:870-83). The polypeptide ring binds with the anionic phosphate moieties in the bacterial cell membrane, displacing $Ca^{2+}$ and $Mg^{2+}$, which are needed for membrane integrity. This results in increased permeability of the cell membrane causing leakage of cellular contents, leading to cell death (Groisman E A et al., Regulation of polymyxin resistance and adaptation to low-Mg2+ environments. *J Bacteriol* 1997; 179:7040-5). The disruption of membrane integrity also increases the susceptibility of the organism to hydrophilic antibiotics such as rifampicin, carbapenems, glycopeptides and tetracyclines, thus paving the way for both gram-negative and gram-positive antimicrobial synergistic combination therapy (Conrad R S et al., Fatty acid alterations and polymyxin B binding by lipopolysaccharides from *Pseudomonas aeruginosa* adapted to polymyxin B resistance. *Antimicrob Agents Chemother* 1989; 33:1724-8).

The development of additional combinations of antibiotics that can be used in the treatment of bacterial infections will add to the arsenal of therapeutic options available to clinicians. The present application is directed to this and other important goals.

BRIEF SUMMARY

In a first embodiment, the present invention is drawn to a method of treating a bacterial infection in a subject, comprising administering a combination comprising oritavancin, or a salt thereof, and a polymyxin, or a salt thereof, to a subject having a bacterial infection, wherein the combination has a synergistic therapeutic effect on the infection greater than the therapeutic effect of either oritavancin or the polymyxin administered alone. In aspects of this embodiment, the antibacterial agents of the combination (i.e., oritavancin, or salt thereof, and the polymyxin, or salt thereof) may be administered in either order, sequentially or concurrently, with overlapping or non-overlapping periods of administration. The antibacterial agents may be administered via the same or different modes of administration.

In a second embodiment, the present invention is drawn to a method of treating a bacterial infection in a subject, comprising administering a concurrent combination comprising oritavancin, or a salt thereof, and a polymyxin, or a salt thereof, to a subject having a bacterial infection, wherein the combination has a synergistic therapeutic effect on the infection greater than the therapeutic effect of either oritavancin or the polymyxin administered alone. In aspects of this embodiment, the antibacterial agents of the combination (i.e., oritavancin, or salt thereof, and the polymyxin, or salt thereof) are administered to the subject in the same mixture and via the same mode of administration.

In a third embodiment, the present invention is drawn to a method of treating a bacterial infection in a subject, comprising administering a sequential combination comprising oritavancin, or a salt thereof, and a polymyxin, or a salt thereof, to a subject having a bacterial infection, wherein the combination has a synergistic therapeutic effect on the infection greater than the therapeutic effect of either oritavancin or the polymyxin administered alone. In aspects of this embodiment, the antibacterial agents of the combination (i.e., oritavancin, or salt thereof, and the polymyxin, or salt thereof) may be administered in either order with overlapping or non-overlapping periods of administration. The antibacterial agents may be administered via the same or different modes of administration.

In certain aspects of each embodiment, the method comprises administering a single dose of oritavancin, or the salt thereof, over a course of therapy to a subject. In these aspects, one, two, three, four, five or more doses of a polymyxin is administered to the subject over the course of therapy.

In certain aspects of each embodiment, the method comprises administering a single dose of a polymyxin over a course of therapy to a subject. In these aspects, one, two, three, four, five or more doses of oritavancin is administered to the subject over the course of therapy.

In certain aspects of each embodiment, combinations comprise at least about 400 mg oritavancin, between about 400 mg to about 1800 mg oritavancin, or about 800 mg, 900 mg, 1000 mg, 1100 mg, 1200 mg, 1300 mg or 1400 mg oritavancin, or a pharmaceutically acceptable salt thereof.

In certain aspects of each embodiment, combinations comprise at least about 200 mg polymyxin, between about 100 mg to about 1800 mg polymyxin, or about 200 mg, 300 mg, 400 mg, 500 mg, 600 mg, 700 mg, 800 mg, 900 mg, or 1000 mg polymyxin.

In each embodiment and aspect of the invention, the polymyxin may be polymyxin A, polymyxin B, polymyxin C, polymyxin D, or polymyxin E (colistin). In preferred embodiments and aspects, the polymyxin is polymyxin B or polymyxin E (colistin). As used herein polymyxin E (colistin) includes colistin sulfate and colistimethate sodium (colistin methanesulfonate sodium, colistin sulfomethate sodium).

Each of the methods of the present invention is preferably practiced wherein the antibacterial agents are administered via intravenous administration, topical or oral administration.

The methods of the present invention include those where the bacterial infection is a Complicated Skin and Skin Structure Infection (cSSSI) or an Acute Bacterial Skin and Skin Structure Infection (ABSSSI). The methods of the present invention also include those where the infectious bacteria and the bacteria causing a bacterial infection is one or more selected from the group consisting of a gram-positive bacteria, *Staphylococcus aureus*, methicillin-resistant *Staphylococcus aureus*, vancomycin-resistant *Staphylococcus aureus*, vancomycin-intermediate *Staphylococcus aureus*, vancomycin hetero-intermediate *Staphylococcus aureus*, *Streptococcus pyogenes*, *Streptococcus agalactiae*, *Streptococcus anginosus*, *Streptococcus intermedius*, *Streptococcus constellatus*, *Streptococcus dysgalactiae*, *Streptococcus dysgalactiae* subsp. *equisimilis*, *Streptococcus pneumoniae*, Group A *Streptococci* species, Group B *Streptococci* species, Group C *Streptococci* species, Group D *Streptococci* species, *Enterococci* species, *Enterococcus faecalis*, vancomycin-resistant *Enterococcus faecalis*, *Enterococcus faecium*, vancomycin-resistant *Enterococcus faecium*, *Staphylococcus epidermidis*, methicillin-resistant *Staphylococcus epidermidis*, *Staphylococcus haemolyticus*, *Bacillus anthracis* and *Clostridium difficile*.

The foregoing has outlined rather broadly the features and technical advantages of the present invention in order that the detailed description of the invention that follows may be better understood. Additional features and advantages of the invention will be described herein, which form the subject of the claims of the invention. It should be appreciated by those skilled in the art that any conception and specific embodiment disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that any description, FIGURE, example, etc. is provided for the purpose of illustration and description only and is by no means intended to define the limits the invention.

BRIEF DESCRIPTION OF THE FIGURES

FIG. 1A, ATCC19606 (reference strain, non-MDR); FIG. 1B, strain 2962406 (MDR); FIG. 1C, strain 2961748 (non-MDR).

DETAILED DESCRIPTION

I. Definitions

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant FIGURE.

As used herein, "antibacterial agents" include oritavancin and salts thereof, as well as one or more polymyxins and salts thereof, including polymyxin A, polymyxin B, polymyxin C, polymyxin D, and polymyxin E (colistin).

As used herein, and unless the context clearly indicates otherwise, the term "oritavancin" includes both the compound itself as well as pharmaceutically acceptable salts thereof, and specifically includes oritavancin diphosphate.

As used herein, and unless the context clearly indicates otherwise, the term "polymyxin" includes both a particular polymyxin (e.g., polymyxin B or polymyxin E) as well as pharmaceutically acceptable salts thereof.

As used herein, a "concurrent combination" is a single formulation comprising a mixture of oritavancin and a polymyxin. As used herein, a "sequential combination" is separate formulations of oritavancin and a polymyxin. The skilled artisan will understand that the methods of the present invention can be practice by either administering a single formulation comprising a mixture of oritavancin and a polymyxin (i.e., a concurrent combination) or administering two separate formulations (i.e., a sequential combination) where a first formulation comprises oritavancin and a second formulation comprises a polymyxin. These two separate means for administering the antibacterial agents takes into account the fact that the two different antibacterial agents may not be physically combined in the same formulation due, for example, to different chemistries of the agents, different modes of administration, or different requirements for carriers and excipients.

II. The Present Invention

Oritavancin

Oritavancin (also termed N-(4-(4-chlorophenyl)benzyl) A82846B and LY333328) has the following chemical structure:

context, as the term "oritavancin" alone may be used for the sake of brevity.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenylsulfonic acid, carbonic acid, succinic acid, citric acid, benzoic acid, acetic acid, and the like. Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counter-ion forming a part of any salt of this invention is not of a critical nature, so long as the salt as a whole is pharmacologically acceptable and as long as the counter-ion does not contribute undesired qualities to the salt as a whole.

Means for the preparation of the glycopeptide antibiotics, including oritavancin and analogs thereof, may be found, for example, in U.S. Pat. No. 5,840,684, incorporated herein by reference in its entirety.

Oritavancin may be used per se in the methods of the present invention, or in the form of a pharmaceutically acceptable salt, hydrate, solvate, or mixtures thereof. The term "pharmaceutically acceptable salt" refers to non-toxic acid addition salts derived from inorganic and organic acids. While reference is made herein to both "oritavancin" and "a pharmaceutically acceptable salt thereof", the term "oritavancin" should be understood to include both the compound per se as well as a pharmaceutically acceptable salt, hydrate, solvate, or a mixture thereof, unless otherwise indicated by Colistin (Polymyxin E)

Colistin (polymyxin E) is a polymyxin antibiotic produced by certain strains of *Bacillus polymyxa* var. *colistinus*. Colistin is a mixture of cyclic polypeptides colistin A and B that is effective against most Gram-negative bacilli. Two forms of colistin are commercially available, namely, colistin sulfate (colistin methanesulfonate sodium) and colistimethate sodium (colistin sulfomethate sodium). Colistin sulfate is cationic; colistimethate sodium is anionic. Colistin has the following structural formula.

20

Polymyxin B

Polymyxin B is derived from the bacterium *Bacillus polymyxa*. Polymyxin B is a mixture of two closely related compounds, polymyxin B1 and polymyxin B2. It has a bactericidal action against almost all Gram-negative bacilli except the Proteus group. Polymyxins bind to the cell membrane and alter its structure, making it more permeable. The resulting water uptake leads to cell death. Polymyxins are cationic, basic proteins that act as surfactants. The structure of polymyxin B1 is as follows:

The structure of polymyxin B2 is as follows:

Pharmaceutical Compositions

In each of the methods of the present invention, the combinations of antibacterial agents may be administrated to the subject in the form of one or more pharmaceutical compositions. The pharmaceutical compositions of the invention comprise the antibacterial agents, or a pharmaceutically acceptable salt, hydrate, solvate, or a mixture thereof, and a pharmaceutically acceptable carrier or excipient, whether a single antibacterial agent or a combination of two (or more) antibacterial agents. In specific aspects, the pharmaceutical compositions of the invention comprise oritavancin, or a pharmaceutically acceptable salt thereof. In other specific aspects, the pharmaceutical compositions of the invention comprise a polymyxin, or a pharmaceutically acceptable salt thereof. These pharmaceutical compositions make up the "sequential combinations" of the present invention. In further specific aspects, the pharmaceutical compositions of the invention comprise both oritavancin and one or more polymyxins, or pharmaceutically acceptable salts thereof (e.g., the "concurrent combinations" of the present invention).

Pharmaceutically acceptable carriers and excipient are those compounds, solutions, substances or materials that can be used to produce formulations of the antibacterial agents that are suitable for administered to a subject, such as a human. In particular, carriers and excipients of the present invention are those useful in preparing a pharmaceutical composition that is generally safe, non-toxic and neither biologically nor otherwise undesirable and that may present pharmacologically favorable profiles, and includes carriers and excipient that are acceptable for veterinary use as well as human pharmaceutical use. Suitable pharmaceutically acceptable carriers and excipients are well known in art and can be determined by those of skill in the art as the clinical situation warrants. The skilled artisan will understand that diluents are included within the scope of the terms carriers and excipients. Examples of suitable carriers and excipients include dextrose, water, glycerol, ethanol, propylene glycol, polysorbate 80 (Tween-80™), poly(ethylene)glycol 300 and 400 (PEG 300 and 400), PEGylated castor oil (e.g. Cremophor EL), poloxamer 407 and 188, a cyclodextrin or a cyclodextrin derivative (including HPCD ((2-hydroxypropyl)-cyclodextrin) and (2-hydroxyethyl)-cyclodextrin; see, e.g., U.S. patent application publication 20060194717), hydrophilic and hydrophobic carriers, and combinations thereof. Hydrophobic carriers include, for example, fat emulsions, lipids, PEGylated phospholipids, polymer matrices, biocompatible polymers, liposheres, vesicles, particles, and liposomes. The terms specifically exclude cell culture medium. More particularly: (1) 5% (w/v) dextrose, or (2) water (e.g., sterile water; Water-For-Infection), may be used as a pharmaceutically acceptable carrier.

Excipients included in a formulation have different purposes depending, for example on the nature of the drug, and the mode of administration. Examples of generally used excipients include, without limitation: stabilizing agents, solubilizing agents and surfactants, buffers, antioxidants and preservatives, tonicity agents, bulking agents, lubricating agents, emulsifiers, suspending or viscosity agents, inert diluents, fillers, disintegrating agents, binding agents, wetting agents, lubricating agents, antibacterials, chelating agents, sweeteners, perfuming agents, flavoring agents, coloring agents, administration aids, and combinations thereof. The pharmaceutical compositions may contain common carriers and excipients, such as cornstarch or gelatin, lactose, sucrose, microcrystalline cellulose, kaolin, mannitol, dicalcium phosphate, sodium chloride, alginic acid, croscarmellose sodium, and sodium starch glycolate.

The particular carrier, diluent or excipient used will depend upon the means and purpose for which the active ingredient is being applied.

Pharmaceutically acceptable excipients also include tonicity agents that make the composition compatible with blood. Tonicity agents are particularly desirable in injectable formulations.

Acceptable methods for preparing the pharmaceutical compositions according to the invention are known to those skilled in the art. For example, pharmaceutical compositions may be prepared following conventional techniques of the pharmaceutical chemist involving steps such as mixing, granulating, and compressing when necessary for tablet forms, or mixing, filling, and dissolving the ingredients as appropriate, to give the desired products for various routes of administration.

Modes of Administration

The pharmaceutical compositions and the antibacterial agents of the present invention may be formulated, for example, for oral, enteral, sublingual, intranasal, intraocular, rectal, intravaginal, transdermal, mucosal, topical or parenteral administration. Parenteral modes of administration include without limitation, intradermal, subcutaneous (s.c., s.q., sub-Q, Hypo), intramuscular (i.m.), intravenous (i.v.), intraperitoneal (i.p.), intra-arterial, intramedullary, intracardiac, intra-articular (joint), intrasynovial (joint fluid area), intracranial, intraspinal, and intrathecal (spinal fluids). Any known device useful for parenteral injection or infusion of drug formulations can be used to effect such administration. In certain aspects of each of the embodiments of the invention, the pharmaceutical composition is administered to the subject intravenously.

Formulations for parenteral administration can be in the form of aqueous or non-aqueous isotonic sterile solutions, suspensions or fat emulsions. The unit dosage of these solutions or suspensions can be in a concentrated liquid, powder or granular form for ex tempore reconstitution in the appropriate pharmaceutically acceptable carrier, such as sterile water, at the time of delivery. In addition to the above-mentioned excipients, powder forms optionally include bulking agents (e.g. mannitol, glycine, lactose, sucrose, trehalose, dextran, hydroxyethyl starch, ficoll and gelatin), and cryo or lyoprotectants. In an alternative embodiment, the parenteral unit dosage form of pharmaceutical compositions and the antibacterial agents of the present invention can be a ready-to-use solution of the pharmaceutical compositions and the antibacterial agents in a suitable carrier in sterile, hermetically sealed ampoules or in sterile pre-loaded syringes. The suitable carrier optionally comprises any of the above-mentioned excipients. The parenteral form used for injection must be fluid to the extent that easy syringability exists.

Excipients used in parenteral preparations may also include, without limitation, stabilizing agents (e.g. carbohydrates, amino acids and polysorbates, such as 5% dextrose), solubilizing agents (e.g. cetrimide, sodium docusate, glyceryl monooleate, polyvinylpyrolidone (PVP) and polyethylene glycol (PEG)), surfactants (e.g. polysorbates, tocopherol PEG succinate, poloxamer and Cremophor™), buffers (e.g. acetates, citrates, phosphates, tartrates, lactates, succinates, amino acids and the like), antioxidants and preservatives (e.g. BHA, BHT, gentisic acids, vitamin E, ascorbic acid, sodium ascorbate and sulfur containing agents such as sulfites, bisulfites, metabisulfites, thioglycerols, thioglycolates and the like), tonicity agents (for adjusting physiological compatibility), suspending or viscosity agents, antibacterials (e.g. thimersol, benzethonium chloride, benzalkonium chloride, phenol, cresol and chlorobutanol), chelating agents, and administration aids (e.g. local anesthetics, anti-inflammatory agents, anti-clotting agents, vasoconstrictors for prolongation and agents that increase tissue permeability), and combinations thereof.

Parenteral formulations using hydrophobic carriers include, for example, fat emulsions and formulations containing lipids, liposheres, vesicles, particles and liposomes. Fat emulsions include in addition to the above-mentioned excipients, a lipid and an aqueous phase, and additives such as emulsifiers (e.g. phospholipids, poloxamers, polysorbates, and polyoxyethylene castor oil), and osmotic agents (e.g. sodium chloride, glycerol, sorbitol, xylitol and glucose). Liposomes include natural or derived phospholipids and optionally stabilizing agents such as cholesterol.

In intravenous (IV) use, a sterile formulation of the pharmaceutical compositions of the present invention and optionally one or more additives, including solubilizers or surfactants, can be dissolved or suspended in any of the commonly used intravenous fluids and administered by infusion. Intravenous fluids include 5% dextrose in water.

In intramuscular preparations, a sterile formulation of the pharmaceutical compositions of the present invention can be dissolved and administered in a pharmaceutical diluent such as Water-for-Injection (WFI) or 5% dextrose in water. A suitable insoluble form of the pharmaceutical compositions may be prepared and administered as a suspension in an aqueous base or a pharmaceutically acceptable oil base, e.g. an ester of a long chain fatty acid such as ethyl oleate.

While the antibacterial agents and pharmaceutical compositions can be administered in a systemic manner through the means described above, they may also be administered in a localized manner. For example, the antibacterial agents may be administered directly, such as through a topical composition or directly into a subcutaneous or other form of wound.

Methods of Treatment, Prophylaxis and Prevention

The methods of the invention comprise contacting bacteria with a concurrent combination or a sequential combination of the antibacterial agents that has a synergistic therapeutic effect on the bacteria greater than would be found when the bacteria is contacted with either oritavancin or the polymyxin alone. The concurrent combinations and sequential combinations of antibacterial agents have the effect of both inhibiting cell wall biosynthesis (through the action of oritavancin) and disrupting of the integrity of the bacterial cell membrane (through the action of a polymyxin). The combined effect of the two antibacterial agents is unexpectedly and synergistically greater than what is seen when bacteria are contacted by either antibacterial agent alone.

The contacting may be carried out in vitro (e.g., in biochemical and/or cellular assays), in vivo in a non-human animal, in vivo in mammals, including humans and/or ex vivo (e.g. for sterilization purposes). As used herein, the term "contacting" is meant to broadly refer to bringing a bacterial cell and a molecule of an antibacterial agent into sufficient proximity such that the antibacterial agent can exert an effect on the bacterial cell. The antibacterial agent may be transported to the location of the bacterial cell, or the antibacterial agent may be situated in a location to which the bacterial cell travels or is brought into contact. The skilled artisan will understand that the term "contacting" includes physical interaction between the antibacterial agent and a bacterial cell, as well as interactions that do not require physical interaction.

As used herein, a "subject" means an animal, such as a mammal, including humans, other higher primates, lower primates, and animals of veterinary importance, such as dogs, cats, horses, sheep, goats, and cattle and the like. The subject may have a bacterial infection, may be at risk for developing a bacterial infection, or may be at greater risk than the general population for exposure to infectious bacteria.

As used herein, "bacterial infection" refers to an infection caused by a species or strain of bacteria for which the methods disclosed herein are appropriate. For example, the methods of treatment may be used in the treatment of subjects having one or more of bacterial skin infections, such as complicated skin and skin structure infections (cSSSI), acute bacterial skin and skin structure infections (ABSSSI), and complicated and uncomplicated skin and soft tissue infections (SSTI), including abscesses, ulcers, burns and cellulitis. The methods of treatment also include treatment of one or more of deep bacterial infections, such as major abscess, infected ulcer, major burn, or deep and extensive cellulitis. Further bacterial infections that may be treated using the methods of the present invention include one or more of bacteremia, i.e., blood stream infections (BSI), catheter-related blood stream infections (CRBSI), endocarditis, osteomyelitis, prosthetic joint infections, pneumonia (community acquired and nosocomial), joint space infections and device infections (e.g., infections associated with pace makers and internal cardiac defibrillators). The methods of treatment can also be practiced concomitantly with surgical intervention for the bacterial infection.

The infectious bacteria and those bacteria causing bacterial infections that may be treated or prevented via the compositions and methods of the present invention include those described in U.S. Pat. No. 5,840,684, gram-positive bacteria, and in particular, *Staphylococcus aureus* (methicillin-susceptible and -resistant strains; vancomycin-susceptible, -intermediate, -hetero-intermediate and -resistant strains), *Streptococcus pyogenes, Streptococcus agalactiae, Streptococcus anginosus* grp. (including *S. anginosus, S. intermedius*, and *S. constellatus*), *Streptococcus dysgalactiae* (including *S. dysgalactiae* subsp. *equisimilis*), *Streptococcus pneumoniae, Streptococci* species, including *Streptococci* Group A species, *Streptococci* Group B species, *Streptococci* Group C species, and *Streptococci* Group D species, *Enterococci* species, *Enterococcus faecalis* (vancomycin-susceptible and -resistant strains), *Enterococcus faecium* (vancomycin-susceptible and -resistant strains), *Staphylococcus epidermidis* (methicillin-susceptible and -resistant strains), *Staphylococcus haemolyticus, Bacillus anthracis*, and *Clostridium difficile* (both vegetative form and spores).

Administration frequencies for the concurrent combinations and sequential combinations of the present invention will vary based on the identity of the antibacterial agent(s) in the concurrent combination or sequential combination, method being practiced, the physical characteristics of the subject, the severity of the subject's symptoms, the form of the infection, the identity of the bacteria, and the formulation and the means used to administer the antibacterial agents. However, administration frequencies will generally include 4, 3, 2 or once daily, every other day, every third day, every fourth day, every fifth day, every sixth day, once weekly, every eight days, every nine days, every ten days, bi-weekly, monthly and bi-monthly. In certain aspects, the concurrent combination or sequential combination is administered once daily. The duration of treatment will be based on the condition being treated and will be best determined by the attending physician. Under some conditions, treatment will be continued for a number of days, weeks, or months. Under other conditions, complete treatment will be achieve through administering one, two or three dose of the concurrent combination or sequential combination over the entire course of treatment. In certain aspects, complete treatment can be achieved using a single dose of the concurrent combination or sequential combination.

Methods of Treating

As discussed in the summary of the invention above, the invention is directed to methods of treating bacterial infections in a subject. Thus, the invention includes methods of treating bacterial infections in a subject, comprising administering a concurrent combination or a sequential combination comprising oritavancin, or a salt thereof, and a polymyxin, or a salt thereof, to a subject having a bacterial infection, wherein the combination has a synergistic therapeutic effect on the infection greater than the therapeutic effect of either oritavancin or the polymyxin administered alone.

The terms "treating" and "treatment" mean at least the mitigation of a bacterial infection, or a disease condition or symptom associated with a bacterial infection in a subject that is achieved by a reduction of growth, replication, and/or propagation, or death or destruction of bacteria, on or in the subject. The terms "treating" and "treatment" include curing, healing, inhibiting, relieving from, improving and/or alleviating, in whole or in part, the bacterial infection or associated disease condition or symptom. The mitigation of a bacterial infection or associated disease condition or symptom may be about 100%, 99%, 98%, 97%, 96%, 95%, 90%, 80%, 70%, 60%, 50%, 40%, 30%, 20%, 10%, 5% or 1% in the subject, versus a subject to which the concurrent combination or sequential combination has not been administered. In one aspect, treating means reducing the population of bacteria causing the infection in the subject to an undetectable level, where detection is by any conventional means, such culturing a sample in the laboratory. In another aspect, treating means complete healing of the infection, shown by an absence of clinical symptoms associated with the infection. In a further aspect of the invention, treating means the mitigation of a bacterial infection or associated disease condition or symptom by at least about 90% in the subject. In an additional aspect, treating means the mitigation of a bacterial infection or associated disease condition or symptom by at least about 95% in the subject.

The amount of oritavancin and the polymyxin sufficient to have a synergistic effect on a bacterial infection will vary, for example, in view of the physical characteristics of the subject, the severity of the subject's symptoms, the form of the infection, the identity of the bacteria, the formulation and the means used to administer the drug, and the method being practiced. The specific dose for a given subject is usually set by the judgment of the attending physician. However, in each dose a synergistically-effective amount of oritavancin is typically between about 100 mg and 3000 mg, between about 400 mg to about 1800 mg, between about 500 mg to about 1600 mg, between about 600 mg to about 1400 mg, between about 800 mg to about 1200 mg, between about 1000 mg to about 1400 mg, or between about 1100 mg to about 1400 mg oritavancin.

In certain aspects, a synergistically-effective amount of oritavancin is about 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950 or 2000 mg oritavancin. In specific aspects, the dose contains about 800, 900, 1000, 1100, 1200, 1300 or 1400 mg oritavancin.

In certain other aspects, a synergistically-effective amount of oritavancin is at least about 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950 or 2000 mg oritavancin. In a preferred aspect, the dose contains at least about 400 mg oritavancin.

In each dose a synergistically-effective amount of a polymyxin is typically between about 100 mg and 3000 mg, between about 200 mg to about 1200 mg, or between about 250 mg to about 1000 mg of the polymyxin.

In certain aspects, a synergistically-effective amount of a polymyxin is about 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, or 1800 mg of the polymyxin. In specific aspects, the dose contains about 200, 300, 400, 500 or 600 mg of the polymyxin.

In certain other aspects, a synergistically-effective amount of polymyxin is at least about 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950 or 2000 mg of the polymyxin. In a preferred aspect, the dose contains at least about 200 mg of the polymyxin.

Depending on the means of administration, the dose may be administered all at once, such as with an oral formulation in a capsule, or slowly over a period of time, such as with an intravenous administration. For slower means of administration, the administering period can be a matter of minutes, such as about 5, 10, 15, 20, 25, 30, 35, 40, 45, 50, 55, 60, 65, 70, 75, 80, 85, 90, 95, 100, 105, 110, 115, 120 or more minutes, or a period of hours, such as about 0.5, 1, 1.5, 2, 2.5, 3, 3.5, 4, 4.5, 5 or more hours. The administration of the dose may be interrupted, such as where the dose is administered via intravenous infusion and the dose is divided into two or more infusion bags. Under such circumstances, the administration of the dose may be interrupted while the infusion bags are changed.

As used herein, the terms "dose", "unit dose", "dosage", "effective dose" and related terms refer to physically discrete units that contain a predetermined quantity of active ingredient calculated to produce a desired therapeutic effect. A single dose is thus a predetermined quantity of an antibacterial agent that is administered to a subject. Preferably, as disclosed in the methods of the invention, the antibacterial agents are formulated as pharmaceutical compositions for administration to the subject.

As used herein, the term "course of therapy" depends on the particular method of the invention, however the term generally means the period of time within which or over which a selected goal is achieved. In terms of methods of treatment, the course of therapy is the time period which is required to achieve treatment of the bacterial infection in the subject.

Although the invention is preferably directed to the treatment of bacterial infections, the invention encompasses therapeutic and prophylactic methods against other diseases caused by or related to bacterial infection, including but not limited to otitis, conjunctivitis, pneumonia, bacterial infections, sinusitis, pleural empyema and endocarditis, intravascular or endothelial infections, osteomyelitis and meningitis. In such methods, the antibacterial agents are administered to a subject in an amount sufficient to provide a therapeutic effect and thereby prevent or treat the infection of the subject.

IV. Examples

Example 1

Activity of Oritavancin Combined with Colistin Against Multi-Drug Resistant Strains of *Acinetobacter baumannii*

Background:

Managing infections caused by multi-drug resistant *Acinetobacter baumannii* (MDRAB) remains a healthcare challenge because of the few therapeutic options available. Combinations of low doses of colistin (COL) with glycopeptides have been shown to act synergistically against MDRAB in vitro. Here, the activity of oritavancin (ORI), a lipoglycopeptide, is described when combined with COL in checkerboard and time-kill assays.

Methods:

Broth microdilution MIC testing (CLSI M07-A9) was performed on the *Acinetobacter baumannii* (AB) reference strain ATCC 19606 (obtained from ATCC) and 10 AB strains, including 8 MDRAB (resistant to ≥3 of the following: beta-lactams, gentamicin, fluoroquinolones and tetracycline; obtained from Eurofins Medinet Chantilly, Va.). The requirement of 0.002% polysorbate 80 (P-80) for testing oritavancin also necessitated the testing of COL in the presence of P80. Checkerboard assays were used to determine activity of antimicrobial combinations; fractional inhibitory concentration indices (FICI) were used to define synergy, indifference or antagonism. Broth macrodilution MICs were determined following conditions used for synergy time-kill assays. Synergy time-kill studies were performed following CLSI guidelines. Synergy was defined as a ≥2 log decrease in colony forming units (CFU)/mL between the combination and its most active constituent at 24 h.

Results:

As shown in Table 1, COL MICs were 4- to 16-fold lower when tested in the presence of P80 versus in its absence. By checkerboard analysis, ORI and COL were synergistic (FICI<0.5) against 7 of the 11 AB strains tested. Furthermore, in synergy time-kill assays, ORI and COL synergized against all 11 of the AB strains tested, including MDRAB (see Table 1).

Conclusions:

ORI shows promising activity in vitro in combination as it synergizes with COL against AB strains including MDRAB, warranting further exploration of this combination as a possible treatment option.

TABLE 1

| | | | Broth macrodilution MICs (µg/mL) | | Concentrations (µg/mL) that yielded synergy in time-kill | |
|---|---|---|---|---|---|---|
| Strain | Phenotype | FICI | ORI | COL | ORI | COL |
| 2691999 | MDR | 0.36 | >8 | 1 | 4 | 0.12 |
| 2692406 | MDR | 0.61 | >8 | 0.25 | 4 | 0.12 |
| 2692650 | MDR | 0.37 | >8 | 0.25 | 4 | 0.12 |
| 2692721 | MDR | 0.49 | >8 | 0.5 | 4 | 0.12 |
| 2693922 | MDR | 0.26 | >8 | 0.5 | 4 | 0.12 |
| 2694038 | MDR | 0.69 | >8 | 0.12 | 4 | 0.06 |
| 2694224 | MDR | 0.35 | >8 | 0.5 | 4 | 0.12 |
| 2694227 | MDR | 0.58 | >8 | 0.5 | 4 | 0.12 |
| 2691748 | Non-MDR | 0.46 | >8 | >16 | 8 | 1 |
| 2691818 | Non-MDR | 0.59 | >8 | 0.25 | 4 | 0.12 |
| ATCC 19609 | Non-MDR | 0.30 | >8 | 0.25 | 4 | 0.06 |

MDR, multi-drug resistant (resistant to ≥3 of the following drugs or class of drugs: beta-lactams, fluoroquinolones, gentamicin, tetracycline)
ORI, oritavancin
COL, colistin
FICI, fractional inhibitory concentration index (<0.5 indicates synergy)

Example 2

Activity of Oritavancin Combined with Colistin Against Multi-Drug Resistant Strains of *Acinetobacter baumannii*

Infections caused by *Acinetobacter baumannii* are increasingly becoming problematic because multi-drug resistant strains are being implicated. Polymyxins and tigecycline have been used to treat such infections but resistance and/or toxicity to these agents are being reported. Combination therapy has been advocated as a means of treating these infections, with in vitro data suggesting synergy between COL and several agents (Hornsey et al., *Antimicrob Agents Chemother* 56:3080-3085, 2012; Vidaillac et al, Antimicrob Agents Chemother 56:4856-4861, 2012; Lee et al., Antimicrob Agents Chemother doi:10.1128/AAC.00703-13, 2013; Ohara et al., Antimicrob Agents Chemother 57:2103-2108, 2013). Here, the activity of oritavancin, a semi-synthetic lipoglycopeptide, is described when combined with COL in checkerboard and time-kill assays against *A. baumannii*.

Strains.

*Acinetobacter baumannii* (AB) reference strain ATCC 19606 was obtained from ATCC. 10 AB strains, including 8 multi-drug resistant (MDR) AB (resistant to ≥3 of the following: beta-lactams, gentamicin, fluoroquinolones and tetracycline), were obtained from Eurofins Medinet (Chantilly, Va.).

Antimicrobial Agents.

Colistin sulfate (hereafter referred to as colistin [COL]; Bergen et al., *Antimicrob Agents Chemother* 50:1953-1958, 2006) was from Sigma Aldrich (Saint Louis, Mich.). Oritavancin diphosphate was from The Medicines Company (Parsippany, N.J.).

Minimum inhibitory concentrations (MICs). Broth microdilution MICs were determined according to CLSI (CLSI document M7-A9, 2013) guidelines with the exception that COL MICs were also determined in the presence of 0.002% polysorbate 80 (P80) since P80 was to be present in the combination tests because of its requirement for testing oritavancin. Broth macrodilution MICs were determined following conditions used for synergy time-kill assays.

Testing of Synergy by Time-Kills.

Time-kill assays followed CLSI guidelines (NCCLS, CLSI document M26-A2, 1999) with the exception that 96 deep-well plates were used. Exponential-phase bacteria were diluted to approximately $5 \times 10^5$ colony-forming units (CFU)/mL and exposed to ORI or COL alone, or in combination in CAMHB containing 0.002% P80. Bacteria were enumerated by serial dilution plating. To prevent drug carryover during serial dilution plating, aliquots of the drug-challenged culture were added to an equal volume of 25 mg/mL activated charcoal suspension. Synergy was defined as a ≥2-log 10 decrease in CFU/mL between the combination and its most active constituent after 24 h (at least one of the drugs must be present at a concentration that does not affect the growth curve of the test organism [aac.asm.org/site/misc/ifora.xhtml]). All experiments were repeated at least two times and a representative experiment is presented in the plots; data points are an average of duplicate CFU/mL determinations within an experiment.

By checkerboard analysis, ORI was found to be synergized with COL against 7 out of the 11 *A. baumannii* strains tested (Table 2).

Figure 1A:
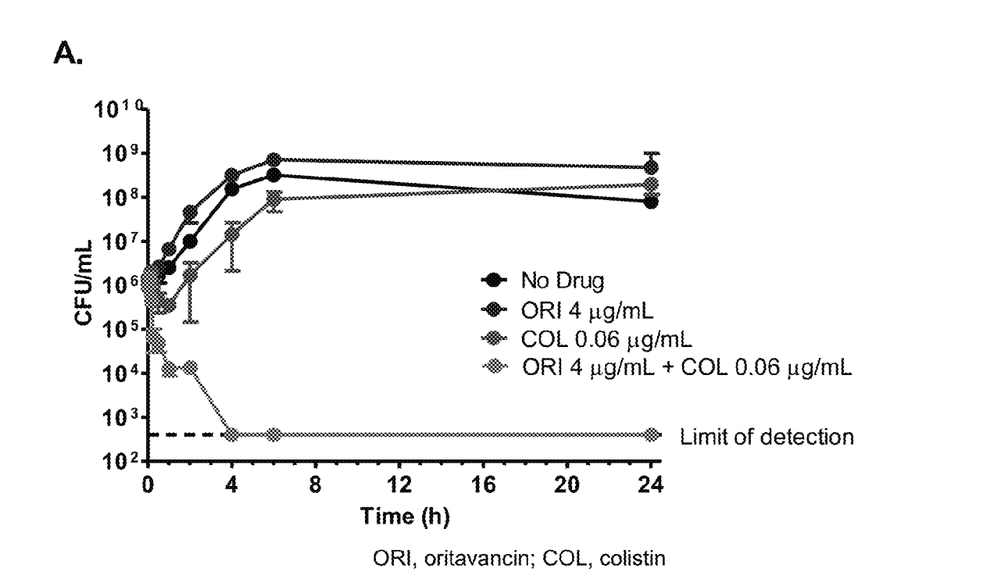
FIGS. 1A-1C. Oritavancin in combination with colistin displays synergistic bactericidal activity against *A. baumannii* strains.
Figure 1B:
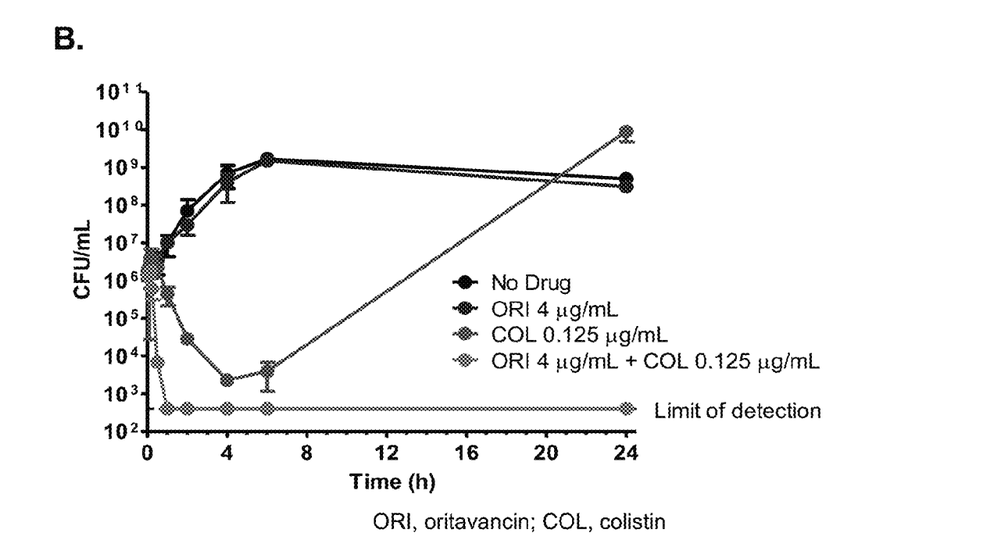
Figure 1C:
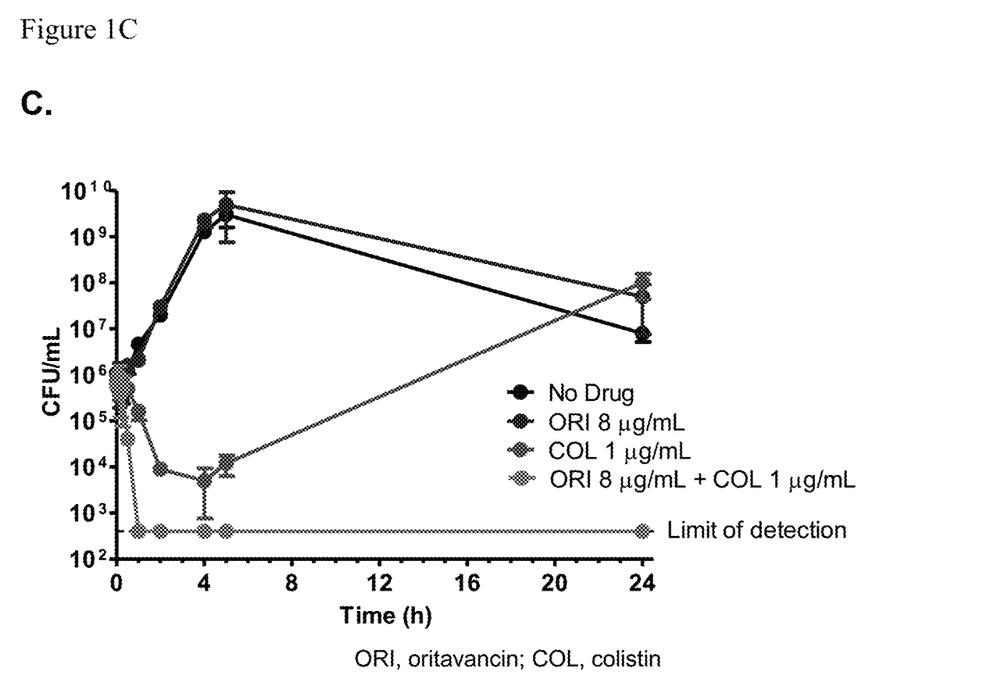

By time-kill analysis, ORI was found to be synergized with COL against all 11 *A. baumannii* strains tested (FIG. 1 and Table 2)

COL MICs against the *A. baumannii* strains were 2 to 16-fold lower when tested in the presence of P80 compared to testing in the absence of P80 (Table 3).

TABLE 2

Fractional inhibitory concentration indices, broth macrodilution MICs, and oritavancin and colistin concentrations that yielded synergy against *A. baumannii* strains.

| Strain | Phenotype | FICI | Synergy by Checkerboard | Broth macrodilution MICs (µg/mL)[a] | | Concentrations (µg/mL) that yielded synergy in time-kill[a] | |
|---|---|---|---|---|---|---|---|
| | | | | ORI | COL | ORI | COL |
| 2691999 | MDR | 0.36 | Yes | >8 | 1 | 4 | 0.12 |
| 2692406 | MDR | 0.61 | No | >8 | 0.25 | 4 | 0.12 |
| 2692650 | MDR | 0.37 | Yes | >8 | 0.25 | 4 | 0.12 |
| 2692721 | MDR | 0.49 | Yes | >8 | 0.5 | 4 | 0.12 |
| 2693922 | MDR | 0.26 | Yes | >8 | 0.5 | 4 | 0.12 |
| 2694038 | MDR | 0.69 | No | >8 | 0.12 | 4 | 0.06 |
| 2694224 | MDR | 0.35 | Yes | >8 | 0.5 | 4 | 0.12 |
| 2694227 | MDR | 0.58 | No | >8 | 0.5 | 4 | 0.12 |
| 2691748 | Non-MDR | 0.46 | Yes | >8 | >16 | 8 | 1 |
| 2691818 | Non-MDR | 0.59 | No | >8 | 0.25 | 4 | 0.12 |
| ATCC 19609 | Non-MDR | 0.30 | Yes | >8 | 0.25 | 4 | 0.06 |

MDR, multi-drug resistant (resistant to ≥3 of the following drugs or class of drugs: beta-lactams, fluoroquinolones, gentamicin, tetracycline)
ORI, oritavancin
COL, colistin
FICI, fractional inhibitory concentration index (<0.5 indicates synergy and are in bold; average of 3 independent experiments)
[a]From 2 independent experiments all with identical outcomes Testing of Synergy by Checkerboard Assay.

A microtiter plate checkerboard assay was used to assess synergy between ORI and COL against the *A. baumannii* strains. ORI was tested at concentrations from 0.0015-16 µg/mL while COL was tested at concentrations from 0.008-0.5 µg/mL. Plates were examined for growth in the wells after 24 h incubation at 37° C. Interpretation of checkerboard results was by Fractional Inhibitory Concentration Index (FICI; Bonapace et al., *Diag Microbiol Infec Dis* 38:43-50, 2000) calculation—MIC of ORI in combination with COL/MIC of ORI alone plus MIC of COL in combination with ORI/MIC of COL alone. An FICI of ≤0.5 was considered synergistic. Three independent experiments were performed for each strain.

TABLE 3

Colistin MICs in the absence and presence of Polysorbate 80 (P80) against the *A. baumannii* strains.

| Strain | Phenotype | −P80 | +P80 | Fold change in MIC (−P80/+P80) |
|---|---|---|---|---|
| 2691999 | MDR | 1 | 0.25 | 4 |
| 2692406 | MDR | 2 | 0.125 | 16 |
| 2692650 | MDR | 0.5 | 0.125 | 4 |
| 2692721 | MDR | 1 | 0.25 | 4 |
| 2693922 | MDR | 0.5 | 0.125 | 4 |
| 2694038 | MDR | 1 | 0.25 | 4 |

TABLE 3-continued

Colistin MICs in the absence and presence of Polysorbate 80 (P80) against the *A. baumannii* strains.

| Strain | Phenotype | −P80 | +P80 | Fold change in MIC (−P80/+P80) |
|---|---|---|---|---|
| 2694224 | MDR | 1 | 0.25 | 4 |
| 2694227 | MDR | 1 | 0.125 | 8 |
| 2691748 | Non-MDR | 4 | 0.5 | 8 |
| 2691818 | Non-MDR | 2 | 1 | 2 |
| ATCC 19609 | Non-MDR | 1 | 0.25 | 4 |

MDR, multi-drug resistant (resistant to ≥3 of the following drugs or class of drugs: beta-lactams, fluoroquinolones, gentamicin, tetracycline)
P80, 0.002% polysorbate-80

ORI shows promising activity in vitro in combination as it synergizes with COL against *A. baumannii* strains including those with the MDR phenotype. This warrants further exploration of this combination as a possible treatment option.

COL MIC values against *A. baumannii* in the presence of P80 were lower than those in the absence of P80, suggesting that like ORI (Arhin et al., *Antimicrob Agents Chemother* 52:1597-1603, 2008), COL may bind to plastic surfaces thereby underestimating its potency when it is tested in the absence of P80. The data support the caution raised by Hindler and Humphries (*J Clin Microbiol* 51: 1678-1684, 2013) regarding testing methodology for COL and advocating inclusion of P80.

What is claimed is:

1. A method of treating a bacterial infection in a subject, comprising administering a synergistic combination comprising oritavancin, or a salt thereof, and a polymyxin, or a salt thereof, to a subject having a bacterial infection, wherein the infectious bacteria is a gram-positive bacteria.

2. The method of claim 1, wherein antibacterial agents of the combination are administered sequentially.

3. The method of claim 2, wherein antibacterial agents of the combination are administered via different modes of administration.

4. The method of claim 1, wherein antibacterial agents of the combination are administered concurrently.

5. The method of claim 4, wherein antibacterial agents of the combination are administered to the subject in the same formulation and via the same mode of administration.

6. The method of claim 2, wherein antibacterial agents of the combination are administered with overlapping periods of administration.

7. The method of claim 2, wherein antibacterial agents of the combination are administered via the same mode of administration.

8. The method of claim 1, wherein a single dose of oritavancin is administered to the subject over a course of therapy.

9. The method of claim 8, wherein one, two, three, four, or five doses of a polymyxin is administered to the subject over the course of therapy.

10. The method of claim 1, wherein a single dose of a polymyxin is administered to the subject over a course of therapy.

11. The method of claim 10, wherein one, two, three, four, or five doses of oritavancin is administered to the subject over the course of therapy.

12. The method of claim 1, wherein the polymyxin is polymyxin B or polymyxin E (colistin).

13. The method of claim 12, wherein the polymyxin is colistin sulfate or colistimethate sodium.

14. The method of claim 1, wherein the antibacterial agents are administered via intravenous administration, topical administration, or oral administration.

15. The method of claim 1, wherein the bacterial infection is a Complicated Skin and Skin Structure Infection (cSSSI) or an Acute Bacterial Skin and Skin Structure Infection (ABSSSI).

16. The method of claim 1, wherein the gram-positive bacteria is one or more selected from the group consisting of *Staphylococcus aureus*, methicillin-resistant *Staphylococcus aureus*, vancomycin-resistant *Staphylococcus aureus*, vancomycin-intermediate *Staphylococcus aureus*, vancomycin hetero-intermediate *Staphylococcus aureus*, *Streptococcus pyogenes*, *Streptococcus agalactiae*, *Streptococcus anginosus*, *Streptococcus intermedius*, *Streptococcus constellatus*, *Streptococcus dysgalactiae*, *Streptococcus dysgalactiae* subsp. *equisimilis*, *Streptococcus pneumoniae*, Group A *Streptococci* species, Group B *Streptococci* species, Group C *Streptococci* species, Group D *Streptococci* species, *Enterococci* species, *Enterococcus faecalis*, vancomycin-resistant *Enterococcus faecalis*, *Enterococcus faecium*, vancomycin-resistant *Enterococcus faecium*, *Staphylococcus epidermidis*, methicillin-resistant *Staphylococcus epidermidis*, *Staphylococcus haemolyticus*, *Bacillus anthracis* and *Clostridium difficile*.

17. The method of claim 2, wherein antibacterial agents of the combination are administered with non-overlapping periods of administration.

18. The method of claim 1, wherein the synergistic combination comprises (i) a pharmaceutical composition comprising oritavancin, or a salt thereof, and a pharmaceutically acceptable carrier or excipient; and (ii) a pharmaceutical composition comprising a polymyxin, or a salt thereof, and a pharmaceutically acceptable carrier or excipient.

19. The method of claim 4, wherein antibacterial agents of the combination are administered to the subject in separate formulations.

* * * * *